United States Patent
Wu et al.

(10) Patent No.: US 8,179,132 B2
(45) Date of Patent: *May 15, 2012

(54) METHOD AND SYSTEM FOR INTEGRATING EDDY CURRENT INSPECTION WITH A COORDINATE MEASURING DEVICE

(75) Inventors: Yanyan Wu, Schenectady, NY (US); Thomas James Batzinger, Burnt Hills, NY (US); Nicholas Joseph Kray, Blue Ash, OH (US); Changting Wang, Niskayuna, NY (US); Haiyan Sun, Niskayuna, NY (US); Francis Howard Little, Cincinnati, OH (US); David Paul Lappas, Hamilton, OH (US); David Michael Dombrowski, Loveland, OH (US)

(73) Assignee: General Electric Company, Niskayuna, NY (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/372,881

(22) Filed: Feb. 18, 2009

(65) Prior Publication Data

US 2010/0207619 A1  Aug. 19, 2010

(51) Int. Cl.
*G01N 27/82* (2006.01)

(52) U.S. Cl. ........ 324/238; 324/239; 324/240; 324/241; 324/242; 324/243; 324/244; 324/166; 33/503; 33/556; 73/602; 73/627; 73/633; 702/167

(58) Field of Classification Search ................... 324/238; 33/556; 702/81, 167; 73/620, 627, 633

See application file for complete search history.

(56) References Cited

U.S. PATENT DOCUMENTS

| 7,921,575 | B2 * | 4/2011 | Little et al. ............... 33/503 |
| 2002/0128790 | A1 * | 9/2002 | Woodmansee .......... 702/81 |
| 2003/0233760 | A1 | 12/2003 | Lotze |
| 2005/0276466 | A1 | 12/2005 | Vaccaro et al. |
| 2008/0075227 | A1 | 3/2008 | Christoph et al. |

OTHER PUBLICATIONS

Qu, Yu-fu; Pu, Zhao-bang; Wang, Ya-ai; Liu, Guo-dong; Zhuang, Zhi-tao; Study of Multiple-sensor Three Dimensional Motion Coordinate Measurement Technology; vol. 15, No. 9, Sep. 2004.

Bradley, C.; Sensor Review; vol. 20, Iss. 1, p. 24-30; Bradford:2000.

* cited by examiner

*Primary Examiner* — Huy Q Phan
*Assistant Examiner* — Son Le
(74) *Attorney, Agent, or Firm* — Penny A. Clarke

(57) ABSTRACT

A method for integrating a measurement device for use in measuring a machine component includes providing a coordinate measuring machine (CMM) and combining eddy current (EC) capabilities and CMM capabilities to form an inspection probe. The method further includes installing the inspection probe on the CMM so that the inspection probe measures external boundaries of the machine component with the CMM capabilities and substantially simultaneously measures at least one of internal boundaries, internal defects, surface defects, and material properties of the machine component with the EC capabilities, which are directly linked to actual component dimensional information provided by CMM. The inspection data can be simultaneously linked to and/or displayed with a CAD model to enable a direct comparison between the inspection data and the nominal requirements specified on the CAD model.

20 Claims, 2 Drawing Sheets

METHOD AND SYSTEM FOR INTEGRATING EDDY CURRENT INSPECTION WITH A COORDINATE MEASURING DEVICE

BACKGROUND OF THE INVENTION

The field of the present invention relates generally to inspection probes, and more specifically, to a method of integrating an inspection probe for use in measuring a machine component.

Prior to being placed in service, at least some known rotor blades or other components are measured using measurement probes to ensure that that the blade has the proper dimensions for use in a turbine engine. Often, such blades are inspected via a non-destructive inspection technique to ensure that each blade does not include internal defects and/or surface cracks that may not be visible to the naked eye. Additionally, it is important to measure both the external and internal geometry of the blade.

Coordinate measuring devices, such as coordinate measuring machines (CMMs), have been used for high accuracy, external dimensional measurement. Nondestructive examination (NDE) sensors including ultrasound (UT) sensors, eddy current (EC) sensors, etc., have been used separately to determine a thickness, internal defects, or surface condition measurements. With known systems, the two types of measurements are generally done separately. In some other applications, the NDE data was scanned along the tool path generated based on a normal CAD model, but have not been linked to nominal CAD model and/or the actual dimensions measured from CMM.

Known methods for measuring a blade generally require two separate processes to inspect both the external/internal geometry, or internal/surface defects of the blade. First, at least some known blades are inspected using computed tomography (CT) and/or ultrasound (UT) to inspect the internal geometry or defects of the blade. An eddy current (EC) sensor is typically used for identifying surface or near surface defects. A coordinate measuring machine (CMM) probe or a laser scanner on a CMM is then used to inspect the external geometry of the blade and for external dimensional measurement. Accordingly, a significant amount of time may be required to complete the setup and inspection process for each individual process of CT, CMM, EC, and/or UT. Moreover, automated UT/EC inspection currently requires a motion control system and, therefore, requires a pre-inspection process or a CAD model to program the system to accurately follow the contour of the blade.

Accordingly, such known inspection methods are generally time-consuming, not suitable for in-situ inspection, and/or expensive. Further, in at least some known inspection systems, the NDE measurement (such as EC) data is not directly linked to the geometry information. For example, if a surface crack is detected by an EC sensor, the location of the defect on the component is not associated to the geometry of the component being inspected. The location of the defects may be critical for deciding the health of a component. For example, if a crack is in a critical region, the component may not be reparable. In addition, the EC probe needs to be maintained in tight contact against the surface contour to ensure that the distance between the EC sensor and the component surface to be inspected is maintained substantially constant to avoid noise. The dimensional information acquired through CMM can be used to guide position EC probe normally and tightly to the contour of the component. For CMM, complicated blade geometry, such as a component having a deep, narrow opening or cavity, generally requires complicated set-ups and/or bending of the CMM probes to measure the cavity geometry.

BRIEF DESCRIPTION OF THE INVENTION

In one aspect, a method for integrating a measurement device for use in measuring a machine component is provided. The method includes providing a coordinate measuring machine (CMM) and combining eddy current (EC) probe capabilities and CMM high-accuracy, dimensional measurement capabilities to form an integrated inspection probe. The method further includes installing the integrated inspection probe on the CMM so that the inspection probe measures external dimensions of the machine component with the CMM capabilities and substantially simultaneously measures at least one of internal wall thickness and surface/subsurface defects of the machine component with the EC capabilities. In addition, proximity sensors can be used to determine the surface normality and a distance between the sensor and the component to be inspected.

In another aspect, a system for measuring a machine component is provided. The system includes a measurement device that includes a coordinate measuring machine (CMM) and an inspection probe that combines eddy current (EC) capabilities and CMM capabilities. In addition, proximity sensors can be used to determine the surface normality and a distance between the sensor and the component to be inspected. The inspection probe is installed on the CMM so that the inspection probe measures external boundaries of a machine component using the CMM capabilities and substantially simultaneously measures a thickness of the machine component using the EC capabilities. In addition, proximity sensors can be used to determine the surface normality and distance between the sensor and the component being inspected. The system further includes a display coupled to the measurement device to facilitate displaying measurement data of defects associated with geometry information from either, or from both, of a CAD model and dimensional measurement data of the machine component.

DETAILED DESCRIPTION OF THE INVENTION

An exemplary embodiment of the invention provides a system for measuring a machine component, such as, but not limited to, a blade. The system includes a measurement probe for measuring the machine component, a closed-loop control and data processing system, and a display for displaying measurements of the machine component together with or without a CAD model. The measurement probe integrates a coordinate measuring machine (CMM) probe with an eddy current probe. The eddy current probe measures a position of at least one surface/sub-surface defect, such as a crack, or at least one material property on that spot, such as the conductivity within the machine component and represents a position of each internal defect with location and dimensional information determined by the CMM probe. In another embodiment, the measurement probe may be a customized inspection probe installed on a CMM machine and having both eddy current sensing and CMM capabilities. In such an embodiment, the eddy current probe is not physically coupled to the CMM probe. In any embodiment, the measurement probe combines the capabilities of eddy current inspection and CMM inspection.

In one embodiment, the measurement probe is configured to simultaneously measure a geometry of at least two sides of the machine component by placing the measurement probe in contact with one of the at least two sides, such as a thin wall structure or a coating layer. In another embodiment, the customized eddy current probe is configured to measure a surface that is substantially normal to the machine component. In the exemplary embodiment, the measurement probe is configured to measure a geometry and surface/subsurface defects of a rotor blade.

It should be noted that although the present invention is described with respect to rotor blades, one of ordinary skill in the art should understand that the present invention is not limited to being used only with rotor blades. Rather, the present invention may be used to measure any electrically conductive machine component in which eddy currents can be induced.

Figure 1:
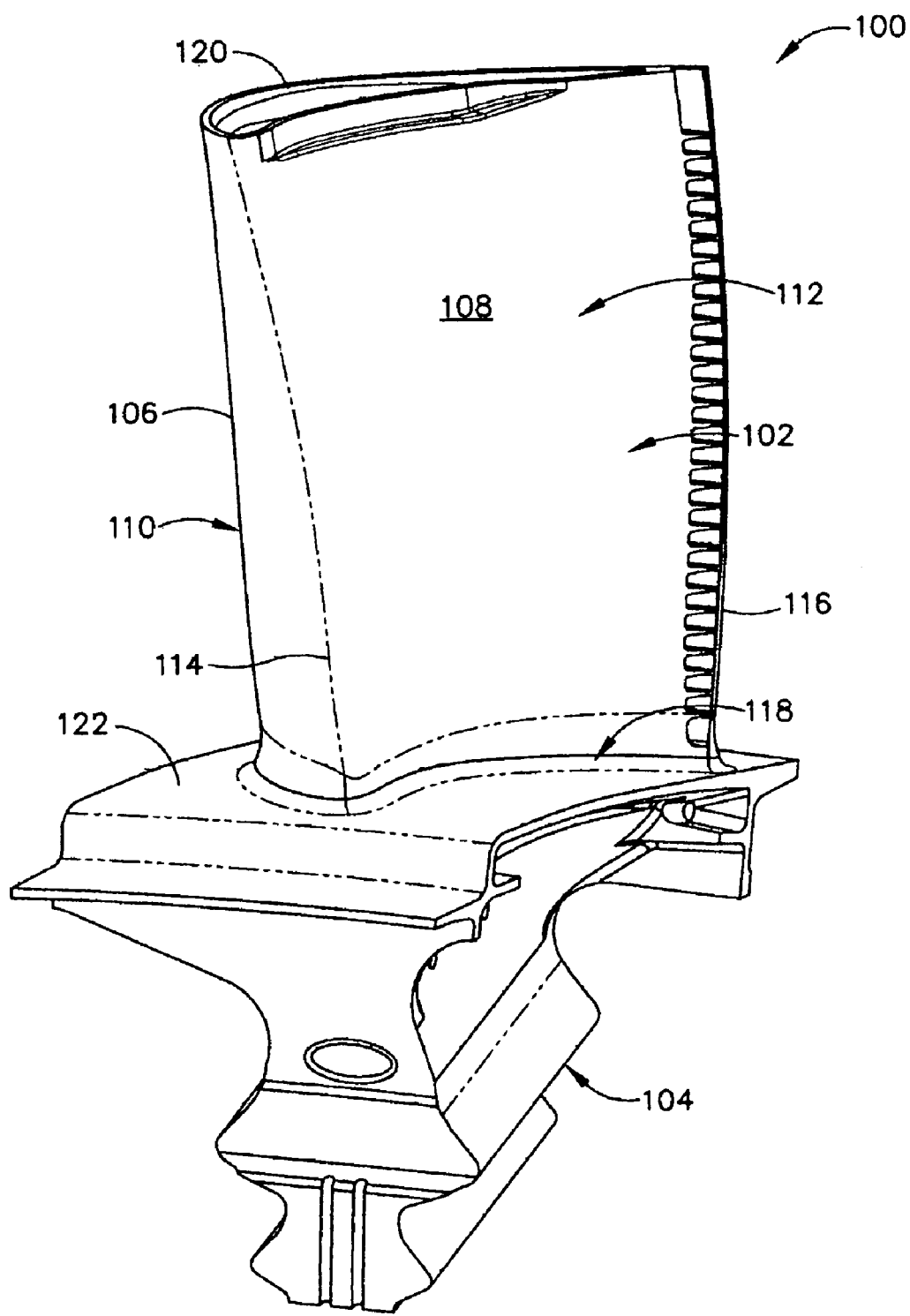
FIG. 1 is an exemplary embodiment of a turbine engine rotor blade.

FIG. 1 is an exemplary embodiment of a turbine engine rotor blade 100. Blade 100 includes an airfoil 102 and an integral dovetail 104 that is used for mounting blade 100 to a rotor (not shown). Blade 100 includes a first contoured sidewall 106 and a second contoured sidewall 108. In the exemplary embodiment, first sidewall 106 is convex and defines a suction side 110 of blade 100, and second sidewall 108 is concave and defines a pressure side 112 of blade 100. Sidewalls 106 and 108 are joined together at a leading edge 114 and at an axially-spaced trailing edge 116 of blade 100. More specifically, airfoil trailing edge 116 is spaced chordwise and downstream from airfoil leading edge 114. First and second sidewalls 106 and 108, respectively, extend longitudinally or radially outward in span from a blade root 118 positioned adjacent dovetail 104, to an airfoil or blade tip 120. A dovetail platform 122 is positioned at blade root 118 and extends radially outward from first and second sidewalls 106 and 108, respectively. It should be noted that blade 100 is exemplary only and the general configuration of blade 100 may take any conventional form, with or without platform 122 or dovetail 104. For example, blade 100 may be formed integrally with a disk in a blisk-type configuration that does not include dovetail 104.

Prior to installing blade 100 within an engine (not shown), and/or during maintenance of the engine, blade 100 is typically inspected using a measurement probe (not shown in FIG. 1) to ensure that that blade 100 is fabricated for and includes the proper dimensions for use in the engine. Further, blade 100 is inspected to ensure that blade 100 does not include internal and/or external defects. Accordingly, during this inspection, it is important to measure both the external and internal geometry and/or defects of the blade.

Figure 2:
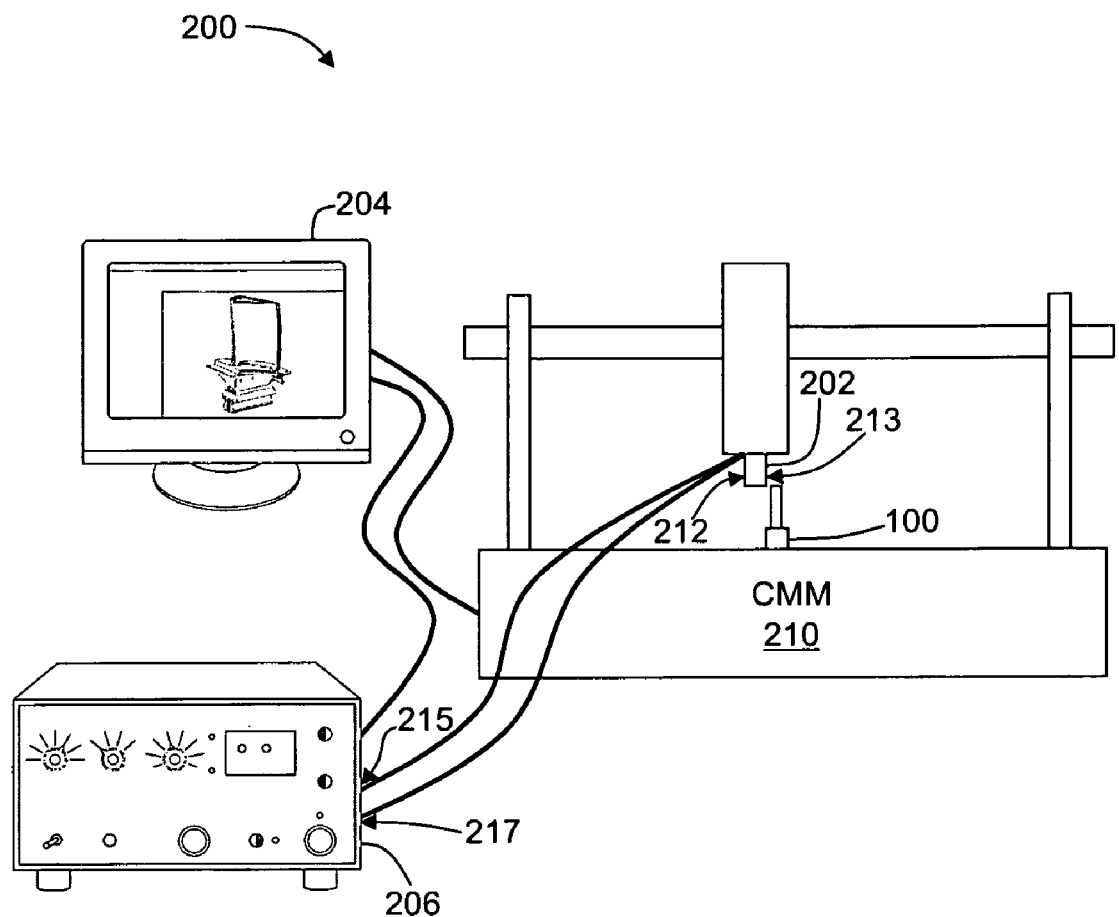
FIG. 2 is an illustration of an exemplary system that may be used to measure the rotor blade shown in FIG. 1.

FIG. 2 is an illustration of an exemplary system 200 that may be used to measure blade 100. In the exemplary embodiment, system 200 includes a measurement probe 202, a display 204, and an impedance measuring device 206. Further, in the exemplary embodiment, measurement probe 202 integrates a coordinate measuring machine (CMM) 210 and an eddy current probe 212. Eddy current probe 212 can be either physically coupled or integrated to a CMM probe 213 such that the integrated probe 202 can measure, substantially simultaneously, the dimensions, defects, and location of the defects of blade 100. Although the exemplary embodiment is described with respect to measurement probe 202 including an eddy current probe 212 coupled to a CMM probe 213, in an alternative embodiment, measurement probe 202 may be a customized inspection probe including an integrated probe installed on CMM machine 210 and having both eddy current capabilities and CMM capabilities without physically coupling an eddy current probe 212 to a CMM probe 213. In any embodiment, measurement probe 202 combines the capabilities of eddy current inspection and CMM inspection. Further, in the exemplary embodiment, each component of system 200 is electrically coupled to a computer and/or a signal detector and/or a controller and/or a processor (not shown). Moreover, although CMM probe 213 and EC probe 212 are illustrated in FIG. 2 as separate components, in one embodiment, CMM probe 213 and EC probe 212 may be integrally formed together. In another embodiment, a unitary probe may be fabricated that includes both CMM and EC capabilities. In addition, proximity sensors (not shown) can be added to the integrated sensor for use in determining the surface normality and a distance between the sensor and the component to be inspected.

In one embodiment, an adaptor (not shown) is used to integrate UT/EC with CMM. In such an embodiment, the adaptor has a mechanical and electrical circuit interface that enables coupling with a CMM index head, and a housing structure that retains EC and/or UT probes, and/or other sensors, such as, but not limited to, a proximity sensor. The adaptor also includes a mechanical or electrical mechanism and/or a proximity sensor that senses and transfers contact information between the integrated probe and the component to be inspected to facilitate preventing a collision between the integrated sensor and component to be inspected. In the exemplary embodiment, CMM system 200 should be able to stop once the integrated probe has a firm contact with the component being inspected. The interface circuit of the adaptor facilitates the transfer of the measurement signal obtained from the sensors through CMM internal cables to the signal receiver or signal trigger, such that the inspection data can be obtained without using additional external cables.

EC probe 212 is connected to eddy current detector 206, which is electrically coupled to display 204. In one embodiment, eddy current probe 212 is also coupled to a signal digitizer and a signal detector (not shown). CMM 210 is also electrically coupled to display 204. In the exemplary embodiment, the control system and data processing system form a closed-loop control. Accordingly measurements received by both CMM probe 213 and eddy current probe 212 and/or the customized inspection probe can be displayed substantially simultaneously on display 204. The closed loop control system and data processing system may be used to position/orient the integrated probe 202 to facilitate maintaining probe 202 in a correct orientation and in tight contact against the component contour, and to link the dimensional/positional measurement data with defect inspection data.

During operation, measurement probe 202 is used to inspect blade 100 by receiving measurements from CMM machine 210 and eddy current probe 212 substantially simultaneously. During inspection, CMM machine 210 is used to determine a position of eddy current probe 212 in terms of location and an orientation of probe 212, as well as providing dimensional information of the component inspected. Substantially simultaneously, eddy current probe 212 is used to determine a thickness of blade 100 and/or a position of any internal defects within blade 100 by inducing eddy currents within the material of blade 100 and measuring the eddy currents using eddy current detector 206. In the exemplary embodiment, the thickness of the blade includes, but is not limited to, the distance between the suction side 110 (shown in FIG. 1) and pressure side 112 (shown in FIG. 1) of blade 100 and/or the distance between an outer surface of blade 100 and an internal passage defined therein. Accordingly, in the exemplary embodiment, the thickness and/or position of defects is combined with dimensional information measured from measurement probe 212. As such, the external boundaries and dimensions of blade 100, the internal boundaries and dimensions of blade 100, and any internal defects within blades 100, and/or the corresponding CAD model of the component, are displayed at real-time during the inspection process on display 204. In one embodiment, the nominal geometry, dimensions, and defects are displayed in real-time 3-dimensional imaging.

During operation, system 200 eliminates a need to position CMM probe 213 within deep and narrow cavities of blade 100. Rather, the cavity geometry is measured from an external surface of blade 100 using measurement probe 202. Further, in the exemplary embodiment, measurement probe 202 is only required to travel along either the pressure side 112 or the suction side 110 of blade 100 to measure the complete blade geometry on both sides. Accordingly, an amount of time required for the measurement is reduced. Moreover, the signal from eddy current probe 212 is sensitive to surface normal. Accordingly, the surface normal as measured by eddy current probe 212 can be used as a reference of surface normality for CMM probe 213.

In one embodiment, a method is provided for integrating a measurement device for use in measuring a machine component. The method includes providing a coordinate measuring machine (CMM). The method also includes combining eddy current capabilities and CMM capabilities to form an inspection probe. The inspection probe is installed on the CMM so that the inspection probe measures external boundaries of the machine component with the CMM capabilities and substantially simultaneously measures internal boundaries of the machine component with the eddy current capabilities. In the exemplary embodiment, the measurement probe is coupled to a display to facilitate displaying measurements and/or nominal geometry information of the machine component.

In one embodiment, the inspection probe is configured to determine a position of at least one surface/sub-surface defect within the machine component using the eddy current capabilities. In another embodiment, the inspection probe is configured to determine a location of the inspection probe using the CMM capabilities, and represent the position of the at least one internal defect with the determined locations with or without relating the defect information to dimensional information of the component. In one embodiment, the inspection probe is configured to measure thin wall or layer thickness or properties of the machine component by placing the measurement probe in contact with only one side. In the exemplary embodiment, the inspection probe is configured to measure a geometry of a rotor blade.

The above-described systems and methods facilitate providing a more timely and accurate inspection of both the external and internal structures of a machine component. The above-described systems and methods also facilitate the generation of real-time 3-dimensional information and the accurate acquisition of defect information (including the type, size, position, etc.) of the machine component, and linking such defect information to dimensional information and/or a CAD model of the component. Inspection tool path was either generated based on a CAD model or can be adjusted at real time based on the data from proximity sensors. Accordingly CMM productivity is improved, especially when measuring complicated geometries. Further, the above-described systems and methods facilitate providing simple probe compensation for the CMM with an eddy current sensor. It also enables an accurate inspection on a component whose as-built shape has a large deviation from its nominal geometry. Accordingly, the CMM has an increased capability of making internal measurements and surface and/or sub-surface defect measurements.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments of systems and methods for integrating a measurement probe are described above in detail. The systems and methods illustrated are not limited to the specific embodiments described herein, but rather, components of the system may be utilized independently and separately from other components described herein. Further, steps described in the method may be utilized independently and separately from other steps described herein.

While the invention has been described in terms of various specific embodiments, it will be recognized that the invention can be practiced with modification within the spirit and scope of the claims.

What is claimed is:

1. A method for integrating a measurement device for use in measuring a machine component, said method comprising:
   providing a coordinate measuring machine (CMM);
   at least one of combining eddy current (EC) capabilities and CMM capabilities to form an inspection probe, and adding proximity sensors to determine a surface normality and a distance between the sensor and the component to be inspected; and
   installing the inspection probe on the CMM so that the inspection probe measures external boundaries of the machine component with the CMM capabilities and substantially simultaneously measures at least one of a surface dimension, an internal dimension, a surface defect, a sub-surface defect, and a material property of the machine component with the EC capabilities.

2. A method in accordance with claim 1, further comprising determining an actual position of at least one internal defect within the machine component using the EC capabilities.

3. A method in accordance with claim 2, further comprising:
   determining at least one of a location of the inspection probe using the CMM capabilities, and the surface normality and distance between the sensor and the component being inspected using the proximity sensors; and
   representing the position of the at least one internal defect or surface defect with the determined location of the component.

4. A method in accordance with claim 1, further comprising measuring a geometry of a rotor blade using the inspection probe.

5. A method in accordance with claim 1, further comprising measuring a geometry of at least two sides of the machine component by placing the inspection probe in contact with one of the at least two sides to be measured.

6. A method in accordance with claim 1, further comprising measuring a surface that is substantially normal to the machine component using the inspection probe.

7. A method in accordance with claim 1, further comprising displaying measurements of the machine component.

8. A measurement device comprising:
   a coordinate measuring machine (CMM); and an inspection probe that combines eddy current (EC) capabilities and CMM capabilities, said inspection probe installed on the CMM so that the inspection probe measures external boundaries of a machine component with the CMM capabilities and substantially simultaneously measures at least one of internal boundaries, surface defects, and sub-surface defects of the machine component with the EC capabilities.

9. A measurement device in accordance with claim 8, wherein a position of at least one internal defect or surface defect within the machine component is measured using the EC capabilities.

10. A measurement device in accordance with claim 9, wherein:
actual location of the inspection probe are determined using the CMM capabilities; and
the position of the at least one internal defect is represented with the actual determined location and with respect to the geometry of the component.

11. A measurement device in accordance with claim 8, wherein said inspection probe is configured to measure a geometry of a rotor blade.

12. A measurement device in accordance with claim 8, wherein said inspection probe is configured to measure at least one of a thickness of a thin wall and a layer structure of the machine component when placed in contact with one of the at least two sides.

13. A measurement device in accordance with claim 8, wherein said inspection probe is configured to measure at least one of a surface and a sub-surface defect that is substantially normal to the machine component.

14. A measurement device in accordance with claim 8, wherein said measurement device is coupled to a display to facilitate displaying measurements of the machine component.

15. A system for measuring a machine component, said system comprising:
a measurement device comprising:
a coordinate measuring machine (CMM); and
an inspection probe that combines eddy current (EC) capabilities and CMM capabilities, said inspection probe installed on the CMM so that the inspection probe measures external boundaries of a machine component with the CMM capabilities and substantially simultaneously measures internal boundaries of the machine component with the EC capabilities; and
a display coupled to said measurement device to facilitate displaying measurements of the machine component.

16. A system in accordance with claim 15, wherein a position of at least one sub-surface defect or surface defect within the machine component is measured using the EC capabilities.

17. A system in accordance with claim 16, wherein:
a location and an orientation of the inspection probe are determined using the CMM capabilities; and
the position of the at least one sub-surface defect is represented with the determined location.

18. A system in accordance with claim 15, wherein said inspection probe is configured to measure a geometry of a rotor blade.

19. A system in accordance with claim 15, wherein said inspection probe is configured to measure a geometry of at least two sides of the machine component when placed in contact with one of the at least two sides.

20. A system in accordance with claim 15, wherein said inspection probe is configured to measure at least one of a surface and a sub-surface defect that is substantially normal to the machine component.

\* \* \* \* \*